(12) United States Patent
Pigg

(10) Patent No.: US 10,973,695 B2
(45) Date of Patent: Apr. 13, 2021

(54) REINFORCED ADHESIVE BACKING SHEET

(71) Applicant: KCI USA, Inc., San Antonio, TX (US)

(72) Inventor: William Pigg, Elvington (GB)

(73) Assignee: KCI USA, INC., San Antonio, TX (US)

( * ) Notice: Subject to any disclaimer, the term of this patent is extended or adjusted under 35 U.S.C. 154(b) by 505 days.

(21) Appl. No.: 15/843,699

(22) Filed: Dec. 15, 2017

(65) Prior Publication Data

US 2018/0125720 A1    May 10, 2018

Related U.S. Application Data

(63) Continuation of application No. 12/810,119, filed as application No. PCT/GB2008/004216 on Dec. 19, 2008, now Pat. No. 10,299,966.

(30) Foreign Application Priority Data

Dec. 24, 2007  (GB) ..................... 0725215

(51) Int. Cl.
*A61F 13/02* (2006.01)
*A61F 13/00* (2006.01)

(52) U.S. Cl.
CPC ........ *A61F 13/023* (2013.01); *A61F 13/0203* (2013.01); *A61F 2013/00263* (2013.01); *Y10T 428/24306* (2015.01); *Y10T 428/24322* (2015.01)

(58) Field of Classification Search
CPC .......... A61L 15/58; A61L 15/26; A61F 13/02; A61F 13/0203; A61F 13/023; A61F 13/0276; A61F 2013/00217; A61F 13/105; A61F 13/00; A61F 2013/00238; A61F 2013/00119; A61F 2013/00868; A61F 2013/00263; Y10T 428/24306; Y10T 428/24322
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Non-Final Office Action in U.S. Appl. No. 12/810,119, dated Aug. 10, 2018 (9 pages).

(Continued)

*Primary Examiner* — Ophelia A Hawthorne
(74) *Attorney, Agent, or Firm* — Foley & Lardner LLP

(57) ABSTRACT

A backing sheet for use in a wound dressing includes a semipermeable continuous film laminated to an adhesive-coated apertured layer. The apertured layer is a solid substrate coated with a medically acceptable adhesive. A method of making a backing sheet for use in a wound dressing includes the steps of: forming an adhesive-coated apertured layer by coating a medically acceptable adhesive onto an apertured solid substrate, followed by laminating the adhesive-coated apertured layer to a semipermeable continuous film.

20 Claims, 2 Drawing Sheets

(56) References Cited

U.S. PATENT DOCUMENTS

| | | |
|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,010,883 A * | 4/1991 | Rawlings ............... A61L 15/26 602/52 |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carlon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,495,229 B1 * | 12/2002 | Carte ............... A61F 13/023 428/40.1 |
| 6,553,998 B2 | 4/2003 | Heaton et al. |
| 6,787,682 B2 * | 9/2004 | Gilman ............. A61F 13/023 602/42 |
| 6,814,079 B2 | 11/2004 | Heaton et al. |
| 8,058,499 B2 | 11/2011 | Silcock et al. |
| 10,299,966 B2 * | 5/2019 | Pigg ................ A61F 13/0203 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0154546 A1 * | 7/2006 | Murphy ............ A61F 13/023 442/286 |
| 2007/0276308 A1 * | 11/2007 | Huey ............ A61F 13/00038 602/42 |
| 2011/0160686 A1 * | 6/2011 | Ueda .............. A61F 13/0203 604/365 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

(56) References Cited

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp: 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp: 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E, M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

REINFORCED ADHESIVE BACKING SHEET

This application is a continuation of U.S. application Ser. No. 12/810,119, entitled "Reinforced Adhesive Backing Sheet," filed Sep. 21, 2010, which claims the priority benefit of PCT Application No. PCT/GB2008/004216, filed Dec. 19, 2008, which claims the priority benefit of United Kingdom Application No. GB 0725215.8, filed Dec. 24, 2007, all of which are incorporated herein by reference in their entirety.

The present invention relates to a reinforced adhesive backing sheet, to methods of making such backing sheets, and to wound dressings comprising such backing sheets.

Many wound dressings comprise a wound contacting portion and a microorganism-impermeable backing sheet that covers the wound contacting portion. The wound-contacting portion, which may comprise several layers, is typically absorbent and may be therapeutic. In use, the backing sheet holds the wound contacting portion of the dressing in contact with the wound, blocks the ingress of microorganisms to the wound, and also prevents leakage of wound exudates from the dressing. In certain embodiments, the backing sheet is substantially coterminous with the wound contacting portion. In other embodiments, the backing sheet is larger than the wound contacting portion, such that a margin having width 1 mm to 50 mm, suitably 5 mm to 20 mm, extends around the wound contacting portion to form a so-called island dressing.

Conventional polymers for forming the backing sheet include polyurethanes and poly alkoxyalkyl acrylates and methacrylates such as those disclosed in GB-A-1280631. Typically, the backing sheet comprises a continuous sheet of a high density blocked polyurethane foam that is predominantly closed-cell. Well known backing sheet materials include the polyurethane films available under the Registered Trade Mark ESTANE.

The backing sheet is frequently coated with a medically acceptable adhesive to bond the backing sheet to the wound contacting portion, and/or to the skin of a patient around the wound. For example, in typical embodiments the backing sheet is adhesive coated at least in a marginal region thereof. As previously described, the backing sheet suitably extends beyond the outer edges of the wound contacting sheet to provide an adhesive-coated margin around the wound contacting sheet for attachment of the dressing to skin around a wound. The adhesive material can be moisture vapour transmitting, for example it may be a hydrogel adhesive. However, the mote commonly used pressure-sensitive adhesives are not moisture vapour transmitting. These adhesives are typically printed onto the backing sheet in a patterned (discontinuous) fashion to allow passage of water vapour through the adhesive layer. The step of printing the adhesive adds expense and complexity to the manufacturing process.

Existing adhesive-coated backing sheets are generally quite thick. This thickness is needed in order to give the sheet sufficient stiffness for convenient handling prior to application to the wound. The adhesive layer is also typically quite thick, for example 100 to 250 g/m$^2$. Where a polyurethane foam backing sheet is used, the adhesive layer should be continuous in order to provide the necessary barrier to microorganisms. These thick materials are relatively expensive, and render the desired oxygen- and moisture-permeability difficult to achieve.

Accordingly, a need exists for adhesive backing sheets for use in wound dressings that combine the advantages of low cost, sufficient stiffness for easy handling, and high moisture vapour permeability.

In a first aspect, the present invention provides a backing sheet for use in a wound dressing, comprising a semipermeable continuous film laminated to an adhesive-coated apertured layer, wherein the apertured layer comprises a solid substrate coated with a medically acceptable adhesive.

In a second aspect, the present invention provides a wound dressing comprising a backing sheet according to the first aspect.

In a third aspect, the present invention provides a method of making a backing sheet for use in a wound dressing, said method comprising the steps of: forming an adhesive-coated apertured layer by coating a medically acceptable adhesive onto an apertured solid substrate, followed by laminating the adhesive-coated apertured layer to a semipermeable continuous film.

The adhesive-coated apertured layer provides stiffness to the backing sheets of the present invention, so that thinner and thus more permeable continuous backing films can be used while maintaining acceptable handling properties. In addition, the lamination of the adhesive-coated apertured layer to the continuous film is simpler than many conventional adhesive coating processes, and allows smaller amounts of adhesive to be used. The adhesive-coated layer is apertured. That is to say, there are apertures in the adhesive-coated layer that are substantially adhesive-free and thereby maintain the moisture- and gas-permeability of the backing sheet, in particular when the adhesive is a conventional medically acceptable pressure sensitive adhesive (i.e. not a hydrogel adhesive).

The term "backing sheet" refers to a flexible, sheet material having a structure that is substantially continuous (on a em scale) so that it can be cut to size to form the outer layer of a wound dressing.

The terms "laminated" and "laminating" refer to bonding of the apertured layer to a surface of the continuous film. Suitably, the bonding is adhesive bonding by means of the adhesive coating on the apertured layer. Suitably, the bonding of the apertured layer to the continuos film is substantially solely by means of said adhesive coating. Suitably, the apertured layer is bonded to the backing sheet over substantially the whole of one side of the apertured layer, i.e. at least about 90% of the area of the apertured layer on one side, is bonded to the backing sheet. Suitably, the continuous film and the apertured adhesive-coated layer are substantially coterminous and bonded together across the whole of their respective areas. This results in a unitary, laminated backing sheet. The laminated backing sheets of the present invention are therefore quite different from conventional wound dressings that may have an apertured, adhesive-coated top sheet bonded to a backing sheet around a margin.

The terms "coated" and "coating" refer to application of a layer of adhesive to the apertured substrate. Suitably, substantially all surfaces of the solid substrate are coated with the same adhesive, for example by dipping the substrate in a liquid adhesive. In other embodiments, front and back surfaces of the solid substrate are coated with adhesive, for example by spraying. Suitably, substantially the whole of the side of the apertured substrate (excluding the apertures) facing the continuous film is coated with adhesive, so as to achieve bonding between the continuous film and the apertured sheet across the whole of that side of the apertured substrate. However, the apertures of the coated substrate are not completely filled with the adhesive, whereby apertures remain in the coated substrate to allow passage of gases.

Suitably, the semipermeable continuous film has a thickness in the range of from about 10 micrometers to about 200 micrometers, for example from about 20 micrometers to about 75 micrometers. In one embodiment, the semipermeable continuous film will have a moisture vapor transmission rate (MVTR) of about 300 to about 5000 g/m$^2$/24 hrs, for example about 500 to about 2000 g/m$^2$/24 hrs at 37.5 humidity difference and 32° C. by ASTM Standard E96-80. Suitable films include Smith & Nephew extruded medical films (EU31, EU65, EU93, EU10, PBA73, PBA105, BNX75) all of which are Polyurethane or polyurethane blends except for BNX75, which is a Polyethylene. Further suitable films are provided by Omniflex USA manufactured from TPU, and breathable films such as Inspire 2301 from Intellicoat- and Arnitel VT3801 from DSM. Suitable foam backing layers are provided by SCAPA and Rogers Corp.

The solid substrate of the apertured layer is suitably a layer or sheet having a low basis weight and thickness. For example, the basis weight may be from about 10 gsm to about 500 gsm, typically from about 20 gsm to about 300 gsm. In certain embodiments, the substrate has apertures arranged in a regular pattern, whereby after coating the apertures retain sufficient open (adhesive-free) area to mimic the use of a printed adhesive layer and allow transport of moisture vapour through the backing layer. Suitably, the apertured layer is laminated across substantially the whole of one surface of the film layer. The adhesive suitably also bonds the apertured layer to the film layer. Suitably, the backing sheet according to the present invention consists essentially of the film layer and the apertured adhesive-coated layer.

The solid substrate layer may for example be an apertured textile material, which may be woven or nonwoven, such as a gauze or an apertured nonwoven textile scrim. Suitable lightweight nonwovens are spunbonded webs or lightweight woven scrims such as those used in swabs.

In other embodiments the solid substrate layer may be a unitary thermoplastic layer, for example a network formed for example by extrusion or molding, or a perforated film produced for example by perforation of continuous films. Suitable substrates of this type include extruded films supplied by Smith and Nephew (CB15, CE15, SN09, H514, H518, H624 and PT20 all of which are Polyethylene except for PT20, which is Polypropylene). Also suitable are the apertured films and extruded nets from Delstar Inc. available under the Registered Trade Marks DELNET and NALTEX. The percent open area of the apertures in the apertured substrate layer is may be from about 1% to about 99%, for example from about 25% to about 90%, suitably from about 30% to about 80%.

The medically acceptable adhesive may be a hydrogel adhesive, but suitably it does not comprise a hydrogel. Suitably, the pressure-sensitive adhesive may be based on acrylate ester copolymers, polyvinyl ethyl ether and/or polyurethane. Polyurethane-based pressure sensitive adhesives are preferred. Pressure sensitive adhesives typically comprise an elastomer dissolved or dispersed in a non-aqueous solvent. Suitable pressure-sensitive adhesives are the polyurethane adhesives available under the registered trade mark LEVAGEL. Also suitable are silicone-based adhesives available from Dow Corning. The adhesive may be applied to the apertured solid substrate layer via any method known on the art. The adhesive may be dissolved or dispersed in a suitable solvent prior to coating onto the substrate. The coated substrate may be squeezed, for example between rollers, after dipping in a bath of the adhesive (and optional solvent) to remove excess adhesive. The rollers may be profiled to provide the adhesive-free apertures in the substrate. The basis weight of the adhesive is regulated by the choice of substrate material, the concentration and viscosity of the adhesive bath in which the network is dipped, and the compression conditions after dipping. Suitably, the basis weight of the adhesive is less than about 100 gsm, for example from about 25 to about 75 gsm. The percent open (adhesive-free) area of the apertures in the adhesive-coated apertured layer is typically from about 1% to about 90%, for example from about 10% to about 60%, suitably from about 25% to about 75%.

In one embodiment, the adhesive backing sheets of the invention will have a moisture vapor transmission rate (MVTR) of about 300 to about 5000 g/m$^2$/24 hrs, for example about 500 to about 2000 g/m$^2$/24 hrs at 37.5 difference and 32° C. by ASTM Standard E96-80. It has been found that such moisture vapor transmission rates allow the wound under the dressing to heal under moist conditions without causing the skin surrounding the wound to macerate.

Suitably, the maximum uncompressed thickness of the backing sheet according to the invention is from about 0.1 mm to about 2 mm, suitably from about 0.2 mm to about 1 mm.

The wound dressing according to the second aspect of the invention may comprise, consist essentially of, and/or consist of the backing sheet according to the invention, optionally with a protective cover sheet covering the surface of the adhesive-coated apertured layer opposite the continuous semipermeable film.

More usually, the wound dressing according to the invention further comprises a wound contacting sheet laminated to at least a region of the surface of the adhesive-coated apertured layer opposite the continuous semipermeable film. Suitably, the dressing is an island dressing, whereby an adhesive margin of the backing sheet extends around the wound contacting sheet. The width of the adhesive margin is suitably from about 5 mm to about 30 mm, for example from about 10 mm to about 20 mm. The width of the margin may be uniform, or it may vary in width, for example the wound contacting sheet may not be centered on the adhesive backing sheet.

The wound contacting sheet may be made up of one or more layers, usually including at least one absorbent layer. The absorbent layer may be any of the layers conventionally used for absorbing wound fluids, serum or blood in the wound healing art, including hydrophilic foams, gauzes, nonwoven fabrics, superabsorbents, hydrogels and mixtures thereof. The basis weight of the absorbent layer may be in the range of about 50 to about 500 g/m$^2$, such as about 100 to about 400 g/m$^2$. The uncompressed thickness of the absorbent layer may be in the range of from about 0.5 mm to about 10 mm, such as about 1 mm to about 4 mm. The free (uncompressed) liquid absorbency measured for physiological saline may be in the range of about 5 to about 30 g/g at 25° C.

Other optional layers of the wound contacting sheet include a liquid-permeable, non-adherent wound contacting (top) layer. One or more of the layers may contain one or more therapeutic agents such as humectants, antimicrobials (e.g. silver as metal or a silver salt), odor-absorbents (e.g. activated charcoal), and therapeutic agents to promote wound healing (e.g. growth factors, protease inhibitors).

The wound facing surface of the dressing is suitably protected by a removable cover sheet. The cover sheet is typically formed from flexible thermoplastic material. Suitable materials include but are not limited to polyesters and polyolefins. Suitably, the adhesive-facing surface of the cover sheet is a release surface. That is to say, a surface that is only weakly adherent to the adhesive on the backing sheet to assist peeling of the adhesive layer from the cover sheet. For example, the cover sheet may be formed from a non-adherent plastic such as a fluoropolymer, or it may be provided with a release coating such as a silicone or fluoropolymer release coating.

The area of the dressing according to this aspect of the invention may vary according to the type and size of wound, but is typically from about 1 cm² to about 500 cm², for example from about 4 cm² to about 100 cm².

Typically, the wound dressing according to the present invention is sterile and packaged in a microorganism-impermeable container. For example, sterilization may be performed by gamma-irradiation after packaging.

The method according to the present invention comprises: coating an apertured solid substrate with a medically acceptable adhesive to form an adhesive-coated apertured layer, followed by laminating the coated apertured layer to a semipermeable continuous film. Suitably, the method is adapted for the manufacture of an adhesive backing sheet according to the invention as defined above. Accordingly, all features described in relation to the first aspect of the invention are applicable to this aspect.

According to the present invention, the apertured layer may be coated for example by spraying or dipping the apertured layer with the adhesive, or with a solution or dispersion of the adhesive in a suitable solvent, followed by drying for example at temperatures of about 25° C. to about 100° C. Suitably, the adhesive-coated apertured layer is then compressed, for example between rollers, to remove excess adhesive. Suitably, the method is performed substantially continuously on continuous webs of the apertured and backing film, followed by cutting the laminate into lengths.

An embodiment of the present invention will now be described further, by way of example, with reference to the accompanying drawing, in which.

Figure 1:
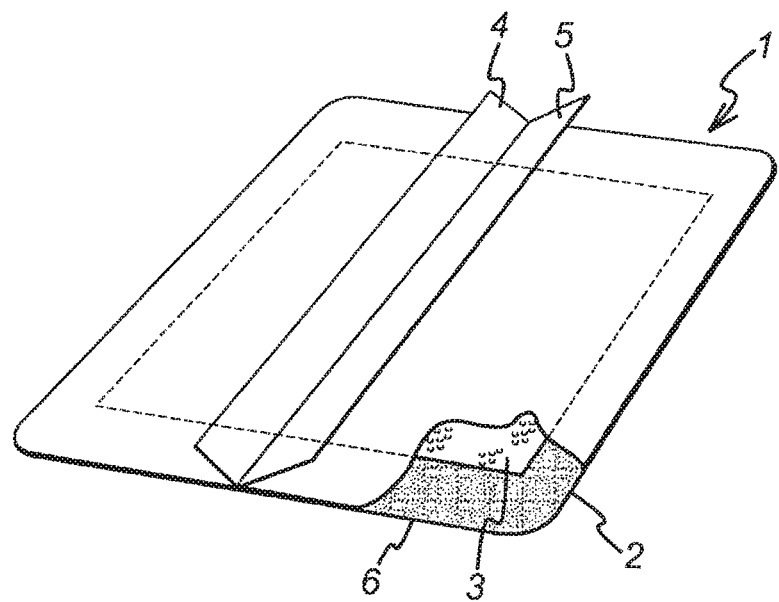
FIG. 1 shows a detail view of part of a backing sheet according to the invention.

Referring to FIG. 1, the wound dressing 1 is an island-type, self-adhesive wound dressing comprising an adhesive backing sheet 2 according to the present invention as described below. The backing sheet 2 is permeable to water vapor, but impermeable to wound exudates and microorganisms.

A wound contacting sheet 3, such as one comprised of absorbent polyurethane foam material of the kind described in EP-A-0541391 and available from Johnson & Johnson Medical Ltd. under the registered trade mark TIELLE, is adhered to a central region of the adhesive-coated backing sheet 2 such that an adhesive-coated margin 6 of the backing sheet extends around the island 2 for attachment of the dressing to the skin around a wound.

Figure 3:
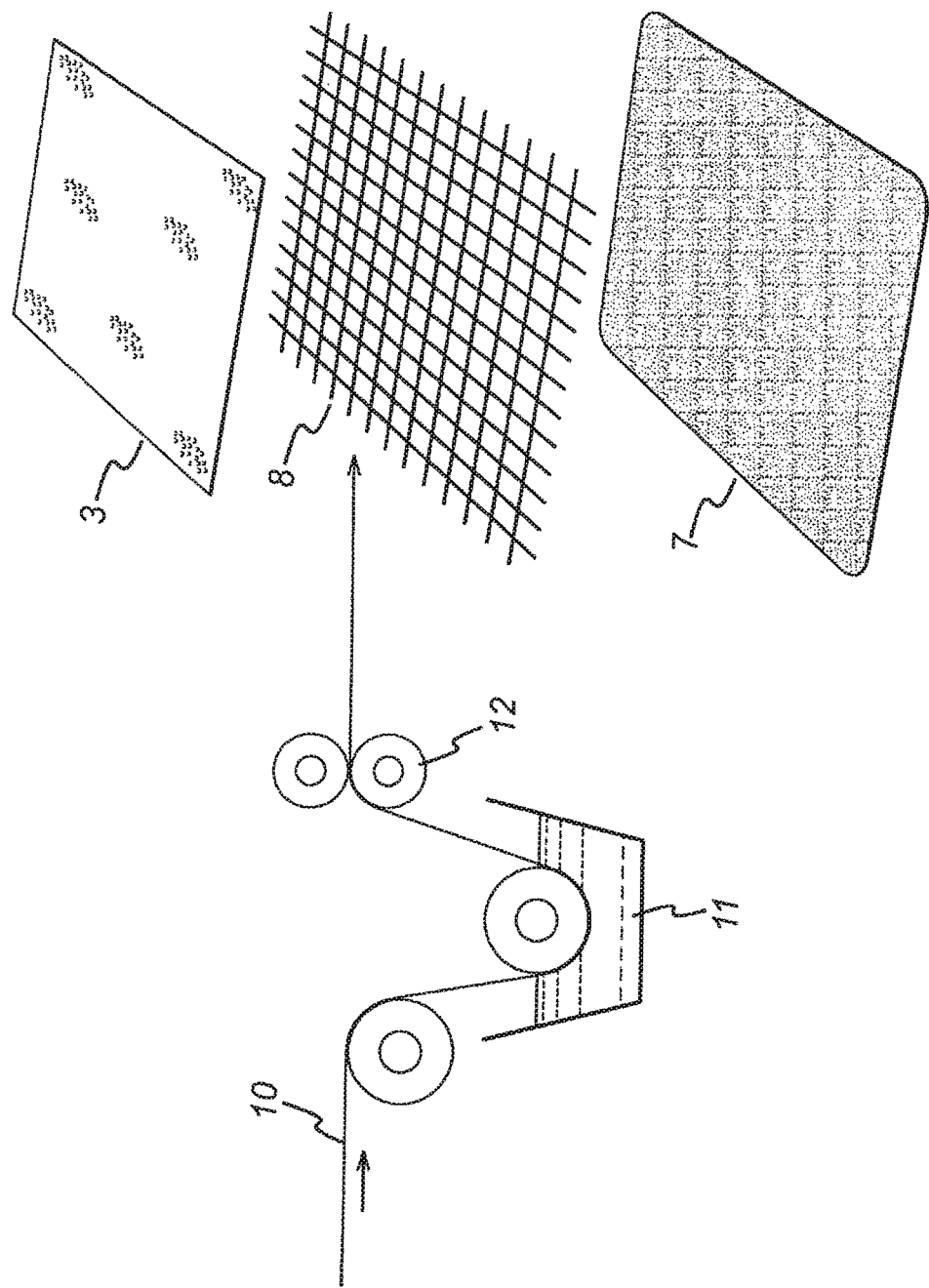
FIG. 3 shows a schematic view of a manufacturing process according to the invention.

Protective release-coated cover sheets 4,5 are provided as shown in FIG. 3. These cover sheets are removed immediately before use of the dressing.

Figure 2:
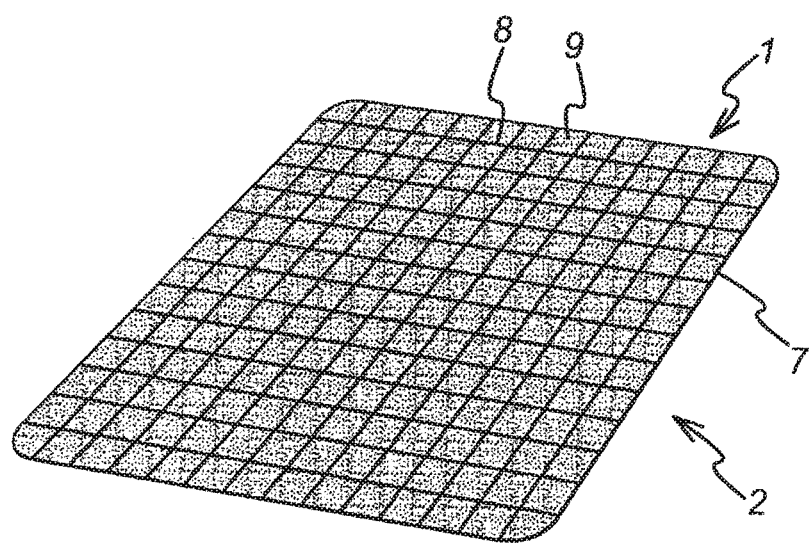
FIG. 2 shows a perspective view of a wound dressing according to the invention.

Referring to FIG. 2, the adhesive-coated backing sheet 2 comprises a continuous, thin, semipermeable polymer film 7 having laminated thereto an adhesive-coated apertured thermoplastic web 8. The strands of the apertured web 8 are coated with a pressure-sensitive, medically acceptable adhesive to bond the apertured web 8 to the polymer film 7, and also to provide the desired adherency and stiffness to the backing sheet 2. Adhesive-free interstices 9 in the apertured web 8 provide the desired moisture- and oxygen-permeability to the backing sheet.

Referring to FIG. 3, one embodiment of the process according to the invention comprises dipping a continuous strip of apertured material 10 in a bath 11 of adhesive, followed by compression between rollers 12 to remove excess adhesive and laminating the coated apertured 8 to the continuous film 7 and the wound contacting island 3.

The entire contents of the patent publications identified above are expressly incorporated herein by reference.

Many other embodiments of the present invention falling within the scope of the accompanying claims will be apparent to the skilled reader.

The invention claimed is:

1. A backing sheet for use in a wound dressing, comprising:
   a continuous film having a first side and a second side and comprising a liquid-impermeable material; and
   a support layer having a first surface and a second surface and comprising a plurality of apertures that each extend through the support layer from the first surface to the second surface, the support layer adapted to be positioned against the first side of the continuous film;
   wherein the support layer further comprises an adhesive material disposed on the first surface and the second surface of the support layer, and wherein the plurality of apertures that extend through the support layer remain substantially free of the adhesive material, and wherein the support layer is adapted to be bound to the first side of the continuous film.

2. The backing sheet of claim 1, wherein the support layer comprises an apertured substrate coated with the adhesive material.

3. The backing sheet of claim 2, wherein the apertured substrate comprises a unitary thermoplastic net.

4. The backing sheet of claim 2, wherein the apertured substrate comprises an apertured textile material.

5. The backing sheet of claim 2, wherein the apertured substrate comprises a woven material.

6. The backing sheet of claim 2, wherein the apertured substrate comprises a nonwoven material.

7. The backing sheet of claim 1, wherein the apertured substrate comprises an apertured nonwoven textile scrim.

8. The backing sheet of claim 1, wherein the basis weight of the adhesive material is less than 100 gsm.

9. The backing sheet of claim 1, wherein a percent open area of the support layer is from about 1% to about 90%.

10. The backing sheet of claim 1, wherein a percent open area of the support layer is from about 10% to about 60%.

11. The backing sheet of claim 1, wherein the continuous film has a moisture vapor transmission rate (MVTR) of between 500 to 2000 g/m²/24 hrs.

12. The backing sheet of claim 1, wherein the adhesive material comprises a hydrogel adhesive.

13. The backing sheet of claim 1, wherein the adhesive material comprises a polyurethane-based pressure sensitive adhesive.

14. The backing sheet of claim 1, wherein the adhesive material comprises a silicone-based adhesive.

15. The backing sheet of claim 1, wherein the continuous film has a thickness of from about 20 micrometers to about 75 micrometers.

16. A backing sheet for use in a wound dressing, comprising:
   a continuous film having a first side and a second side; and an apertured layer having a first side and a second side and comprising a plurality of apertures that each extend through the support layer from the first surface to the second surface, the apertured layer adapted to be positioned against the first side of the continuous film;

wherein the first side and the second side of the apertured layer comprise a silicone-based adhesive, and wherein the plurality of apertures that extend through the support layer remain substantially free of the adhesive material.

17. The backing sheet of claim 16, wherein the continuous film is impermeable to wound exudates and to microorganisms and permeable to water vapor.

18. The backing sheet of claim 16, wherein a percent open area of the apertured layer is from about 10% to about 60%.

19. The backing sheet of claim 16, wherein the continuous film and the apertured layer are substantially coterminous.

20. The backing sheet of claim 16, wherein the continuous film has a thickness of from about 20 micrometers to about 75 micrometers.

\* \* \* \* \*

UNITED STATES PATENT AND TRADEMARK OFFICE
CERTIFICATE OF CORRECTION

PATENT NO. : 10,973,695 B2
APPLICATION NO. : 15/843699
DATED : April 13, 2021
INVENTOR(S) : William Pigg Page 1 of 1

It is certified that error appears in the above-identified patent and that said Letters Patent is hereby corrected as shown below:

In the Claims

Column 6
Line 44, In Claim 7, delete "The backing sheet of claim 1" and insert -- The backing sheet of claim 2 --, therefor.

Signed and Sealed this
Ninth Day of April, 2024

Katherine Kelly Vidal
*Director of the United States Patent and Trademark Office*